(12) United States Patent
Ejiri et al.

(10) Patent No.: US 6,693,204 B2
(45) Date of Patent: Feb. 17, 2004

(54) METHOD FOR PURIFICATION OF CYCLIC ESTER

(75) Inventors: Tetsuo Ejiri, Fukushima (JP); Kazuyuki Yamane, Fukushima (JP); Kentaro Otawara, Fukushima (JP)

(73) Assignee: Kureha Kagaku Kogyo K.K., Tokyo (JP)

( * ) Notice: Subject to any disclaimer, the term of this patent is extended or adjusted under 35 U.S.C. 154(b) by 0 days.

(21) Appl. No.: 10/240,175

(22) PCT Filed: Mar. 30, 2001

(86) PCT No.: PCT/JP01/02721
§ 371 (c)(1), (2), (4) Date: Sep. 30, 2002

(87) PCT Pub. No.: WO01/72736
PCT Pub. Date: Oct. 4, 2001

(65) Prior Publication Data
US 2003/0109722 A1 Jun. 12, 2003

(30) Foreign Application Priority Data
Mar. 31, 2000 (JP) ............................. 2000-096713

(51) Int. Cl.[7] ...................... C07D 319/12; C07D 323/04
(52) U.S. Cl. ...................................... 549/274; 549/267
(58) Field of Search ................................. 549/274, 267

(56) References Cited

U.S. PATENT DOCUMENTS

| | | | |
|---|---|---|---|
| 3,770,386 A | | 11/1973 | Hayashi |
| 4,806,318 A | * | 2/1989 | Saitoh et al. ............... 422/251 |

FOREIGN PATENT DOCUMENTS

| | | |
|---|---|---|
| EP | 0446381 | 9/1991 |
| EP | 0789023 | 8/1997 |
| GB | 2064976 | 6/1981 |
| WO | WO 96/31506 | * 10/1996 |

* cited by examiner

*Primary Examiner*—Ba K. Trinh
(74) *Attorney, Agent, or Firm*—Kanesaka & Takeuchi

(57) ABSTRACT

A method of refining a crystal of a crude cyclic ester comprises the steps of supplying the crude cyclic ester to a vertically extending cylindrical refiner (1) from an inlet (3) provided at a lower part of the refiner (1), agitating the crude cyclic ester by an agitator provided in the refiner (1) to make the crude cyclic ester flow upwardly, refining the crystals of the crude cyclic ester by counterflow-contact between the upflowing crude cyclic ester and a downflowing melted liquid containing a refined crystal component, and taking out refined crystals of the crude cyclic ester from an outlet (4) provided at an upper part of the refiner (1).

12 Claims, 2 Drawing Sheets

METHOD FOR PURIFICATION OF CYCLIC ESTER

TECHNICAL FIELD

The present invention relates to a method of refining a cyclic ester. The cyclic ester is a condensation product of a dicarboxylic acid and diol, or a product made from a hydroxycarboxylic acid dimer which is made circular by dehydrate-condensation. The cyclic ester is used as a starting material for producing a polyester or polyester amide including a biodegraded polymer or medical-use polymer.

BACKGROUND ART

It is well known that the cyclic ester is produced by depolymerizing hydroxycarboxylic acid oligomer. There are two types of crude cyclic esters produced by the conventional method. One is a cyclic ester, wherein no solvent is adhered to its crystal, and the other is a cyclic ester, wherein a high-boiling point organic solvent is adhered to its crystal. The crude cyclic esters are refined by the appropriate method for each of the crude cyclic esters.

The following references describe the manufacturing method for the first-type cyclic ester.

U.S. Pat. No. 2,668,162 describes that a glycolic acid oligomer is reduced to powder and supplied slowly to a reaction vessel, in which it is depolymerized by heating under a super vacuum. Then, the produced gas is cooled for solidification into a crude cyclic ester.

U.S. Pat. No. 4,727,163 describes that a large amount of polyether is block-copolymerized with a small amount of glycolic acid to make a copolymer. The copolymer is heated under a low pressure to be depolymerized. Then, the produced gas is cooled for solidification into the crude cyclic ester.

U.S. Pat. No. 4,835,293 describes that a glycolic acid oligomer is heated into a liquid. The liquid is provided with a flow of nitrogen to increase the surface area so that the liquid is evaporated from the increased surface area. The evaporated gas is provided with a flow of nitrogen and cooled for solidification into a crude cyclic ester.

U.S. Pat. No. 5,326,887 and WO 92/15572A1 describe that a glycolic acid oligomer is heated and depolymerized over a fixed bed catalyst system. Then, produced gas is cooled and solidified into a crude cyclic ester.

The crude cyclic esters produced by the above methods contain impurities such as a hydroxycarboxylic acid oligomer and hydroxycarboxylic acid itself. The crude cyclic esters are purified by re-crystallization using a solvent such as an isopropanol disclosed by European Patent No. 261572, a t-amyl alcohol disclosed by German Patent Publication No. 1808939, a carbon tetrachloride disclosed by German Patent Publication No. 123473904, an ethyl acetate disclosed by U.S. Pat. No. 4,727,163, and an ether disclosed by Japanese Kokai No. 06-172341. A slurry of the crystal produced by the re-crystallization is separated into a solid and a liquid by filtering, cleaned by the solvent used in the re-crystallization process or an other cleaning liquid, and dried to remove the solvent or cleaning liquid, thus providing a purified crystal.

Japanese Kokai No. 09-328481 describes a method of manufacturing the second-type crude cyclic ester, in which a mixture comprising an hydroxycarboxylic acid oligomer and at least one kind of high-boiling point organic solvent having a boiling point between 230° C. and 450° C. is heated under normal or reduced pressure at such a temperature as to depolymerize the oligomer. The depolymerized oligomer is dissolved in the solvent until the remaining rate of the oligomer in the liquid phase reaches 0.5% or less. The heating is further continued at the above temperature to depolymerize the remaining oligomer. The produced cyclic ester is distilled out with the high-boiling point organic solvent, and the crude cyclic ester is recovered from the distilled product.

By the method, the cyclic ester is distilled with at least one organic solvent having a boiling point of 230–450° C., and the crude cyclic ester is collected by cooling the distilled product. In this case, a non-solvent may be added in the distilled product, and the solidified or crystallized cyclic ester is separated into a solid and a liquid. The thus produced crystal of the cyclic ester includes the high-boiling point organic solvent attached thereto, which is difficult to remove by the usual drying method. However, it is indispensable to remove the high-boiling point organic solvent by any method in order to obtain a dried crystal.

A conventional method to remove such a liquid as adhered to the crystal of the cyclic ester is to displace and clean the crystal with a low-boiling point cleaning liquid, such as cyclohexane or ether, and then, remove the low-boiling point cleaning liquid by drying. The drying process is performed at a temperature lower than the melting point of the crystal. Since the cyclic ester sublimates, the loss of the crystal is increased if the pressure is reduced excessively during the drying process. In addition, if necessary, the re-crystallization is performed using an ethyl acetate. Even in this case, the adhered solvent has to be removed by drying. As fully stated above, in the conventional method using the high-boiling point organic solvent, the low-boiling point cleaning liquid is indispensable to displace the liquid adhered to the crystal. As a result, the cleaning liquid waste is a mixture comprising the high-boiling point organic solvent and the low-boiling point cleaning liquid.

The method of refining the first-type of crude cyclic ester requires additional and complicated processes including the processes for drying to remove the solvent or cleaning liquid from the crystal surface, cooling to collect the solvent or cleaning liquid removed during the drying process, evaporating to separate the mixture of the solvent and the cleaning liquid collected during the cooling process. The drying process is performed at a temperature lower than the melting point of the crystal. Also, since the cyclic ester sublimates, the loss of the crystal is increased under excessively reduced pressure. A solvent, such as an alcohol, may bring about ester exchange reaction with the cyclic ester, and re-crystallization is required a few times to remove the impurities caught inside the crystal.

The method of refining the second-type of crude cyclic ester also requires complicated processes including the processes for drying to remove the cleaning liquid adhered to the crystal surface, collecting the cleaning liquid removed during the drying process, and disposing to refine and collect a mixture of the high-boiling point organic solvent and low-boiling point cleaning liquid. A solvent, such as an alcohol, may bring about ester exchange reaction with the cyclic ester, and re-crystallization is required a few times to remove the impurities caught inside the crystal.

Accordingly, it is an object of the present invention to provide a method of refining the crystal of a crude cyclic ester, which is simple and applicable to both the first- and second-types of crude cyclic esters.

DISCLOSURE OF THE INVENTION

According to the present invention, crystal are refined by means of a vertically extending cylindrical refiner provided with an inlet for supplying crude cyclic ester at a lower part of the refiner, and provided with an outlet for taking crystals as a product at an upper part of the refiner, and provided with an agitator for agitating crude cyclic ester in the refiner According to the present invention, a method of refining crystals of a crude cyclic ester comprises the steps of supplying the crude cyclic ester to a vertically extending cylindrical refiner from an inlet provided at a lower part of the refiner, agitating the crude cyclic ester by an agitator provided in the refiner to make the crude cyclic ester flow upwardly, refining the crystals of the crude cyclic ester by counterflow-contact between the upflowing crude cyclic ester and a downflowing melted liquid containing a refined crystal component, and taking out refined crystals of the crude cyclic ester from an outlet provided at an upper part of the refiner.

According to the invention, the crystal of the crude cyclic ester is refined by the counterflow-contact between the upflowing crude cyclic ester and the downflowing melted liquid containing the refined crystal component in the refiner. That is, inventors have found a method that a mother liquid and impurities adhered to the crystal are cleaned off, and those that are taken inside the crystal are sweat off by the counterflow-contact.

BEST MODE FOR CARRYING OUT THE INVENTION

Cyclic Ester

The cyclic ester is a condensation product comprising a dicarboxylic acid diol, or a product made from a hydroxycarboxylic acid dimer which is dehydrate-condensed and made circular. An example of the hydroxycarboxylic acid is a glycolic acid, lactaid acid, 3-hydroxycarboxylic butylic acid, 4-hydroxycarboxylic butylic acid, 3-hydroxycarboxylic valeric acid, or 3-hydroxycarboxylic caproic acid.

In order to provide a finished cyclic ester, it is necessary to refine the first type of cyclic ester having no solvent or the second type of cyclic ester having high-boiling point organic solvent adhered thereto. Each of the refining equipment shown in FIGS. 1 and 2 is useful for both the first and second types of the cyclic esters.

Figure 1A:
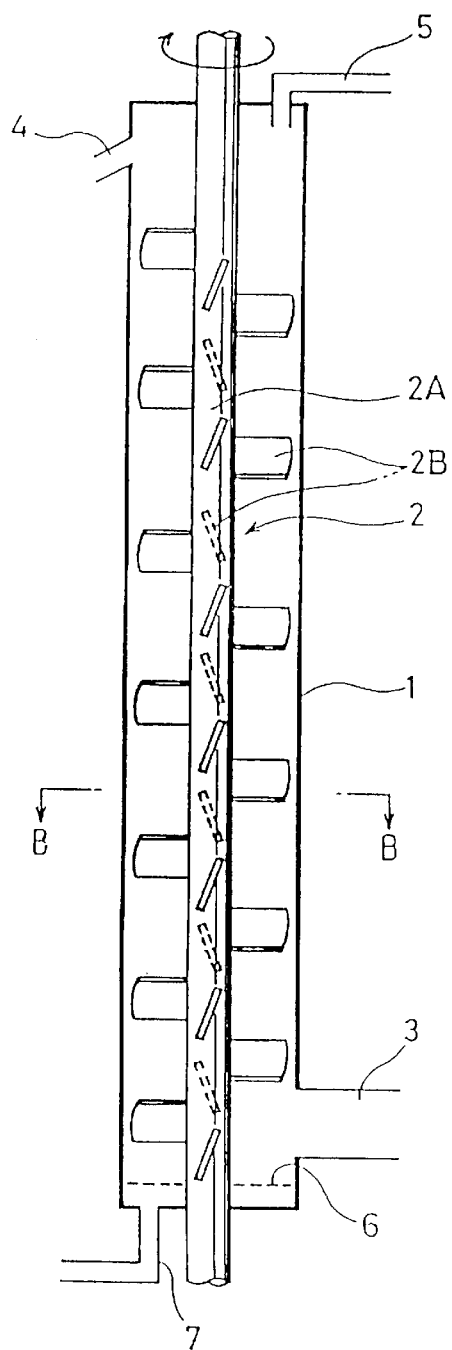
FIG. 1(A) is a vertical section of refining equipment according to an embodiment of the present invention.
Figure 1B:
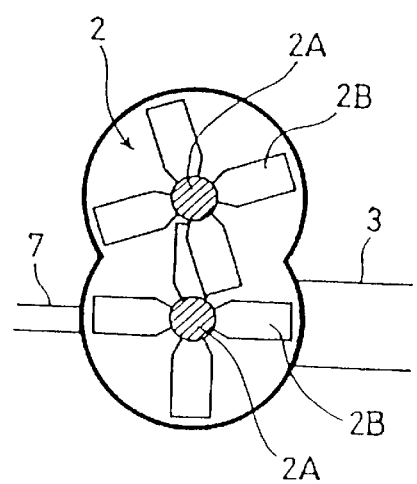
FIG. 1(B) is an enlarged section taken along line B—B in FIG. 1(A).
Figure 2:
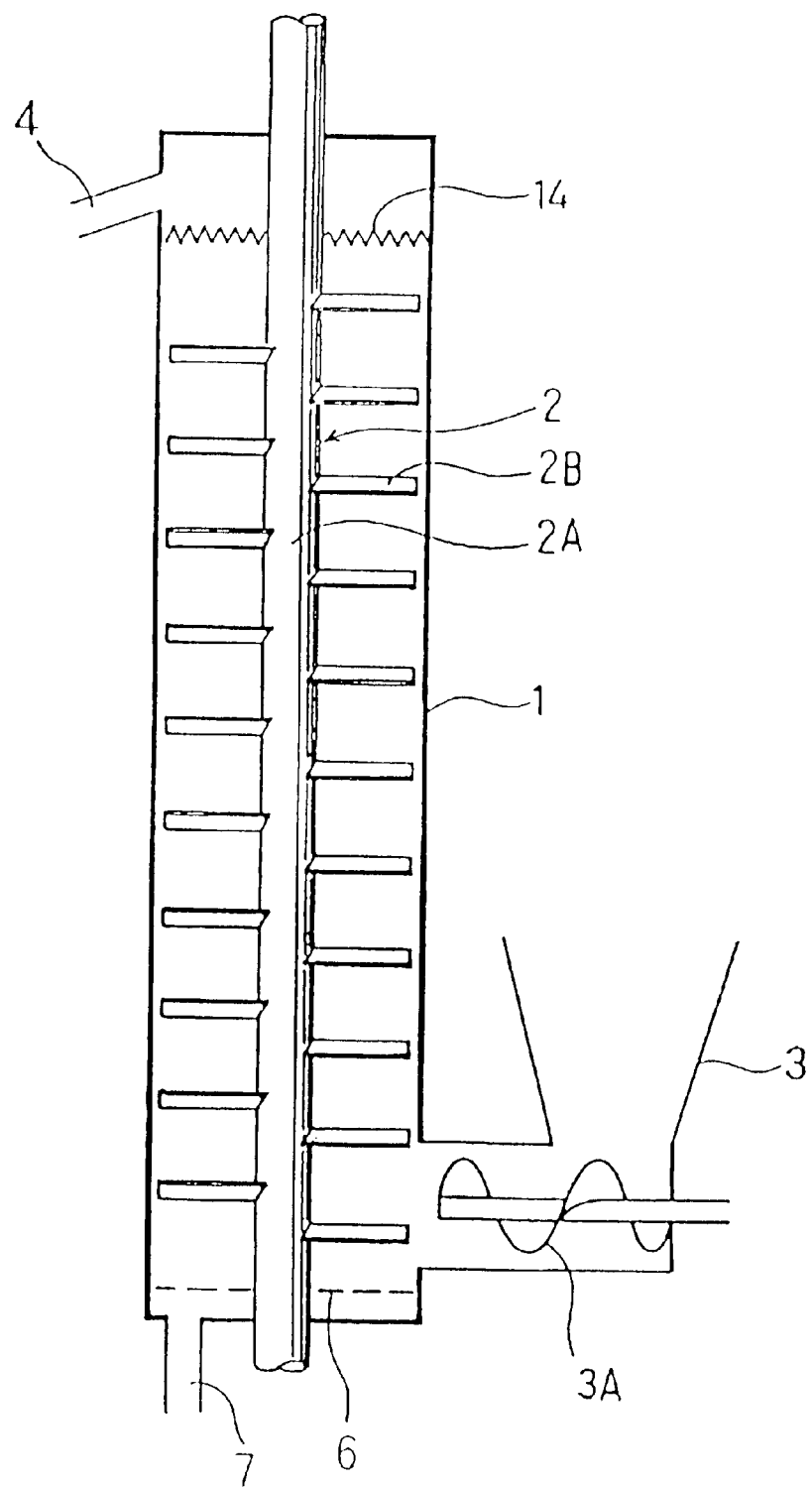
FIG. 2 is a vertical section of of refining equipment according to another embodiment of the present invention.

A cylindrical refiner 1 in FIG. 1(A) extends vertically and is provided with an agitator 2 therein. The agitator 2 comprises, as shown in FIG. 1(B), two rotatable shafts 2A extending vertically and having a plurality of agitating fins 2B. The two rotatable shafts 2A may rotate in the same direction or in opposite directions to each other. In either case, it is preferable that the agitating fins 2B have inclination with respect to the horizontal plane so that they create an upflow of the crude cyclic ester inside the refiner 1 during the rotation of the rotatable shafts 2A. As shown in FIG. 1(B), the agitating fins 2B provided on the two rotatable shafts partly overlap each other when viewed from the top. The overlapped area of the agitating fins 2B increases the agitating capability.

The refiner 1 is provided with an inlet 3 at lower part thereof to supply a crude cyclic ester. The inlet 3 is furnished with a means for supplying the crude cyclic ester to the inside of the refiner 1, such as a screw conveyer (not shown).

The refiner 1 is also provided at an upper part thereof with an outlet 4 to take out the refined ester crystal and a means 5 for supplying a melted liquid for the refined crystal component from the outside of the refiner 1. The means 5 is a conduit for supplying a predetermined amount of the melted liquid having an accurately known temperature.

The refiner 1 is provided with a filter 6 at a lower part thereof and an impurity outlet 7 at the bottom thereof.

The other type of refiner in FIG. 2 has the same reference numbers as those of FIG. 1.

A upright type refiner 1 in FIG. 2 is provided at a lower part thereof with an inlet 3 having a screw conveyer 3A therein to supply a crude cyclic ester including impurities and, at an upper part thereof, a melting heater 14 to melt the ester crystal. The melted liquid melted by the heater 14 are brought into counterflow-contact with the cyclic ester coming upwardly in the refiner 1 to refine the crystal. The refined crystal is taken out from an outlet 4 provided at an upper part of the refiner 1. An agitator 2 of the refiner 1 is provided with a rotatable shafts 2A having agitating fins 2B, unraveling and making the crystal supplied from the inlet 3 flow upwardly.

How to refine the two types of crude cyclic esters using either of the refiners in FIGS. 1 and 2 will be described.

(1) The Cyclic Ester Having No Solvent

The cyclic ester crystal obtained by depolymerizing a hydroxycarboxylic oligomer is successively supplied to the refiner 1 from the inlet 3 by the supplying means such as the screw conveyer. The supplied crystal is agitated by the agitating fins 2B and flows upwardly inside the refiner 1. A part of the crystal turns to a downflowing melted liquid together with the melted cyclic ester, which is melted by the melting heater 14 or supplied from the outside by the melted liquid supplying means 5. The downflowing melted liquid is brought into counterflow-contact with the upflowing crude cyclic ester crystal to clean off the impurities adhered to the surface of the crystal and sweat out the impurities caught inside the crystal, thus refining the crude cyclic ester. The refined crystal is taken out from the outlet 4, and the removed impurities are exhausted from the impurity outlet 7 through the filter 6.

(2) The Cyclic Ester Having High-Boiling Point Organic Solvent Adhered Thereto

The cyclic ester crystal having a high-boiling point organic solvent adhered thereto is obtained by depolymerizing and distilling a hydroxycarboxylic oligomer with the high-boiling point organic solvent, cooling a distilled product at a temperature lower than the melting point of the cyclic ester, and separating the thus produced product, which comprises the cyclic ester crystal and a slurry of the high-boiling point organic solvent, into a solid and a liquid. The thus obtained cyclic ester crystal is successively supplied from the inlet 3 by the supplying means such as the screw conveyer. It is preferable that the content of the cyclic ester crystal in the supplied substances is more than 50%. The supplied crystal is agitated by the agitating fins 2B and flows upwardly inside the refiner 1. A part of the crystal turns to a downflowing melted liquid together with the melted cyclic ester, which is melted by the melting heater 14 or supplied from the outside by the melted liquid supplying means 5. The downflowing melted liquid is brought into counterflow-contact with the upflowing crude cyclic ester crystal to clean off the impurities adhered to the surface of the crystal and sweat out the impurities caught inside the crystal, thus refining the crude cyclic ester. The refined crystal is taken out from the outlet 4 and removed impurities are exhausted from the impurity outlet 7 through the filter 6.

EXAMPLE

As an example, 18.3 kg/hour of a glycolide having a purity rate of 99.99% is obtained by supplying 22.1 kg/hour of a mixture comprising 91.1 mass % of a glycolide and 8.9 mass % of dibutyl phtalate having a boiling point of 340° C. to the refiner 1 shown in FIG. 2, which has two cylinders each having an internal diameter of 75 mm and a height of 2000 mm.

Industrial Application

The present invention comprises the steps of supplying the crud cyclic ester to a vertically extending cylindrical refiner from an inlet provided at a lower part of the refiner, agitating the crude cyclic ester by an agitator provided in the refiner to make the crude cyclic ester flow upwardly, refining the cystal of the crude cyclic ester by counterflow-contact between the upflowing crude cyclic ester and a downflowing melted liquid which contains a refined crystal component, and taking out the refined crystal of the crude cyclic ester from an outlet provided at upper part of the refiner. Consequently, the present invention has the following advantages.

(1) No additional solvent or cleaning liquid for the refining process is required, unlike the conventional refining method.

(2) Since no additional solvent or cleaning liquid is used, the refining equipment is simplified. That is, various processes including cleaning of the high-boiling point organic solvent, evaporation and separation of the high-boiling point organic solvent and the cleaning liquid, drying of removing the cleaning liquid adhered to the refined crystal, cooling and collecting of the cleaning liquid discharged from the drying equipment are not required. Accordingly, many machines and ancillary facilities such as a pump, storage tank, and pipe are not necessary. In addition, electricity, steam, and cooling water are saved.

(3) Even if impurities are caught inside the crystal, and a plurality of times of re-crystallization are required under the conventional method, highly pure crystal is produced by the invention.

(4) Since the steps of the whole process are successively operated, the operation control is easy.

(5) The manufacturing cost is reduced.

What is claimed is:

1. A method of refining a crystal of a crude cyclic ester, comprising the steps of:

supplying said crude cyclic ester to a vertically extending cylindrical refiner from an inlet provided at a lower part of said refiner;

agitating said crude cyclic ester by an agitator provided in said refiner to make said crude cyclic ester flow upwardly;

refining said crystal of said crude cyclic ester by counterflow-contact between said upflowing crude cyclic ester and a downflowing melted liquid which contains a refined crystal component; and taking out said refined crystal of said crude cyclic ester from an outlet provided at an upper part of said refiner.

2. The method according to claim 1, wherein said melted liquid is supplied from outside of said refiner.

3. The method according to claim 1, wherein at least one high-boiling point organic solvent having a boiling point greater than a melting point of said crystal of said crude cyclic ester is adhered to said crystal of said crude cyclic ester.

4. The method according to claim 2, wherein at least one high-boiling point organic solvent having a boiling point greater than a melting point of said crystal of said crude cyclic ester is adhered to said crystal of said crude cyclic ester.

5. The method according to claim 1, wherein said cyclic ester is a hydroxycarboxylic acid cyclic ester.

6. The method according to claim 2, wherein said cyclic ester is a hydroxycarboxylic acid cyclic ester.

7. The method according to claim 3, wherein said cyclic ester is a hydroxycarboxylic acid cyclic ester.

8. The method according to claim 4, wherein said cyclic ester is a hydroxycarboxylic acid cyclic ester.

9. The method of according to claim 5, wherein said hydroxycarboxylic acid cyclic ester is a glycolic acid dimeric cyclic ester.

10. The method of according to claim 6, wherein said hydroxycarboxylic acid cyclic ester is a glycolic acid dimeric cyclic ester.

11. The method of according to claim 7, wherein said hydroxycarboxylic acid cyclic ester is a glycolic acid dimeric cyclic ester.

12. The method of according to claim 8, wherein said hydroxycarboxylic acid cyclic ester is a glycolic acid dimeric cyclic ester.

* * * * *